(12) United States Patent
Zhao et al.

(10) Patent No.: US 11,512,049 B2
(45) Date of Patent: Nov. 29, 2022

(54) PLEUROMUTILIN 2-[(DIPHENYLMETHYL)THIO] ACETIC ACID ESTER WITH ANTI-DRUG RESISTANT BACTERIA ACTIVITY AND A METHOD OF PREPARING THE SAME

(71) Applicants: Qianqian Zhao, Xi'an (CN); Yuqing Zhao, Xi'an (CN); Dan Yang, Xi'an (CN); Jingyi Li, Xi'an (CN); Liang Xin, Xi'an (CN); Ruina Bian, Xi'an (CN); Jie Zhang, Xi'an (CN); Han Li, Xi'an (CN); Bin Tian, Xi'an (CN); Yongbo Wang, Xi'an (CN); Chengyuan Liang, Xi'an (CN); Liang Qi, Xi'an (CN); Gennian Mao, Xi'an (CN)

(72) Inventors: Qianqian Zhao, Xi'an (CN); Yuqing Zhao, Xi'an (CN); Dan Yang, Xi'an (CN); Jingyi Li, Xi'an (CN); Liang Xin, Xi'an (CN); Ruina Bian, Xi'an (CN); Jie Zhang, Xi'an (CN); Han Li, Xi'an (CN); Bin Tian, Xi'an (CN); Yongbo Wang, Xi'an (CN); Chengyuan Liang, Xi'an (CN); Liang Qi, Xi'an (CN); Gennian Mao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 79 days.

(21) Appl. No.: 17/239,582

(22) Filed: Apr. 24, 2021

(65) Prior Publication Data
US 2022/0348540 A1    Nov. 3, 2022

(51) Int. Cl.
C07C 323/52    (2006.01)
A61P 31/04    (2006.01)
C07C 319/28    (2006.01)

(52) U.S. Cl.
CPC ............ C07C 323/52 (2013.01); A61P 31/04 (2018.01); C07C 319/28 (2013.01); *C07C 2601/16* (2017.05); *C07C 2603/84* (2017.05)

(58) Field of Classification Search
CPC . C07C 323/52; C07C 319/28; C07C 2601/16; C07C 2603/84; A61P 31/04
USPC ......................................................... 560/177
See application file for complete search history.

(56) References Cited

U.S. PATENT DOCUMENTS 7,045,524 B2 *    5/2006    Dean .................... C07D 453/04
                                                          544/391

\* cited by examiner

*Primary Examiner* — Ana Z Muresan

(57) ABSTRACT

A compound with anti-drug resistant bacteria activity having the formula (I):

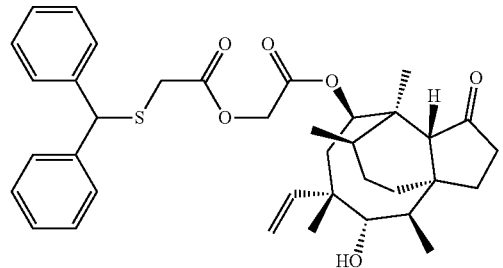

(I) is disclosed. The methods of preparing the compound of formula (I) are also disclosed.

17 Claims, 2 Drawing Sheets

PLEUROMUTILIN 2-[(DIPHENYLMETHYL)THIO] ACETIC ACID ESTER WITH ANTI-DRUG RESISTANT BACTERIA ACTIVITY AND A METHOD OF PREPARING THE SAME

FIELD OF THE INVENTION

The present invention relates to the field of medicinal chemistry, and in particular, to pleuromutilin 2-[(diphenylmethyl)thio]acetic acid ester with anti-drug resistant bacteria activity and a method of preparing the same.

BACKGROUND OF THE INVENTION

Drug-resistant bacteria refer to pathogenic bacteria with drug resistance. Bacterial drug resistance is the main manifestation of pathogen adaptability, and it is also an unavoidable problem in the clinic. In recent years, bacterial drug resistance has occurred worldwide. It is reported that the number of drug-resistant bacteria has been extremely high since the 1990s. People are greatly affected by the problem of bacterial resistance. One factor for the development of drug resistance is the high level of bacteria's own adaptability, which can cause bacteria to develop drug resistance through its genetic genes and mutation factors. In addition to the transformation and conjugation of different types of bacteria, bacteria can obtain drug resistance genes. The overuse of antibiotics is the main reason for the emergence of drug-resistant bacteria. The problem of drug-resistant bacteria has become very prominent.

Solving the problem of bacterial resistance has become a top priority. Pleuromutilin (compound of formula II) is a tricyclic diterpenoid veterinary antibiotic produced in the 1950s from the higher fungi pleurotus pleurotsmutilus and pleurotspasseckerianus strains. It contains 8 chiral carbons and consists of a three-membered ring skeleton of 5-6-8 atoms and a side chain of glycolic acid. It can be used as a starting material or drug intermediate to synthesize antibacterial drugs.

2-[(Diphenylmethyl)thio]acetic acid (CAS:63547-22-8) (compound of formula IV) is a chemical intermediate, which can be used to prepare antibacterial drugs.

The invention modifies pleuromutilin through 2-[(diphenylmethyl)thio]acetic acid structure to obtain a pleuromutilin 2-[(diphenylmethyl)thio]acetic acid ester. Preliminary antibacterial activity experiment shows that the compound has excellent antibacterial activity and has high medical research and application value in the treatment of infectious diseases caused by multi-drug-resistant bacteria.

SUMMARY OF THE INVENTION

In one embodiment, the present invention provides a compound with anti-drug resistant bacteria activity having the following formula (I):

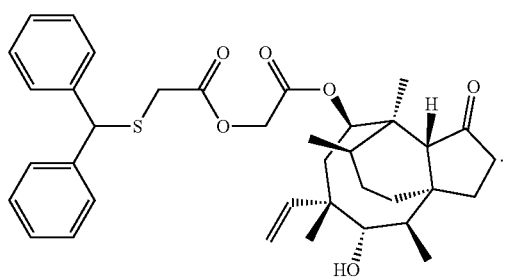

(I)

In another embodiment, a method of preparing the compound of formula (I) includes: reacting a compound of formula (II) with a compound of formula (III) to obtain the compound of formula (I).

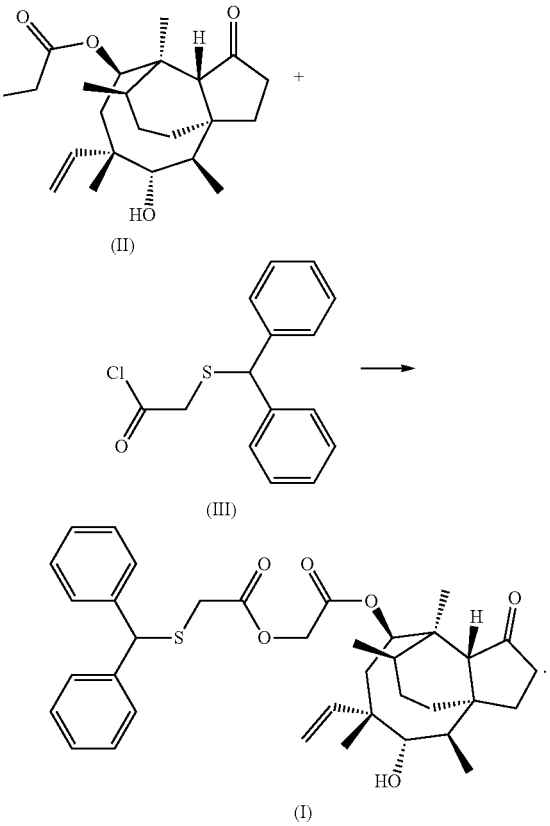

In another embodiment, the reaction of the compound of formula (II) with the compound of formula (III) comprises the following steps: placing the compound of formula (II) and the compound of formula (III), in a molar ratio of 1:1 to 1:1.3, in a reactor; adding an organic solvent and a catalytic amount of triethylamine under nitrogen atmosphere to obtain a reaction mixture; heating the reaction mixture at 20-60° C. for 3-6 hours; extracting the reaction mixture with ethyl acetate to obtain a crude product; and purifying the crude product on a silica gel fresh chromatography column with petroleum ether and ethyl acetate as an eluent to obtain the compound of formula (I).

In another embodiment, the organic solvent is toluene, dichloromethane or N,N-Dimethylformamide.

In another embodiment, the organic solvent is dichloromethane.

In another embodiment, the molar ratio of the compound of formula (II) and the compound of formula (III) is 1:1.1.

In another embodiment, the reaction mixture is heated at 25° C.

In another embodiment, the reaction mixture is heated for 5 hours.

In another embodiment, the eluent is petroleum ether: ethyl acetate=4:1.

In another embodiment, a method of preparing the compound of formula (I) includes reacting a compound of formula (II) with a compound of formula (IV) to obtain the compound of formula (I):

In another embodiment, the reaction of the compound of formula (II) with the compound of formula (IV) comprises the following steps: placing the compound of formula (II), a catalyst, and an ionic liquid in a reactor under nitrogen atmosphere, the catalyst being 12-molybdosilicic acid hydrate ($H_6MouO_{41}Si$); adding the compound of formula (IV) to the reactor to form a reaction mixture; heating the reaction mixture at 20-50° C. for 4-8 hours; placing the reaction mixture in a separating funnel to separate a crude product; purifying the crude product by recrystallization in methanol to obtain the compound of formula (I); and recycling the ionic liquid.

In another embodiment, the ionic liquid is 1-octyl-3-methylimidazolium hexafluorophosphate, 1-hexyl-3-methylimidazolium tetrafluoroborate or 1-butyl-3-methylimidazolium tetrafluoroborate ([BMIM][BF_4]).

In another embodiment, the ionic liquid is the ionic liquid is 1-butyl-3-methylimidazolium tetrafluoroborate.

In another embodiment, the compound of formula (II) and the compound (IV) have a molar ratio of 1:1 to 1:1.3.

In another embodiment, the molar ratio of the compound of formula (II) and the compound of formula (IV) is 1:1.1.

In another embodiment, the reaction mixture is heated at 30° C.

In another embodiment, the reaction mixture is heated for 6 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
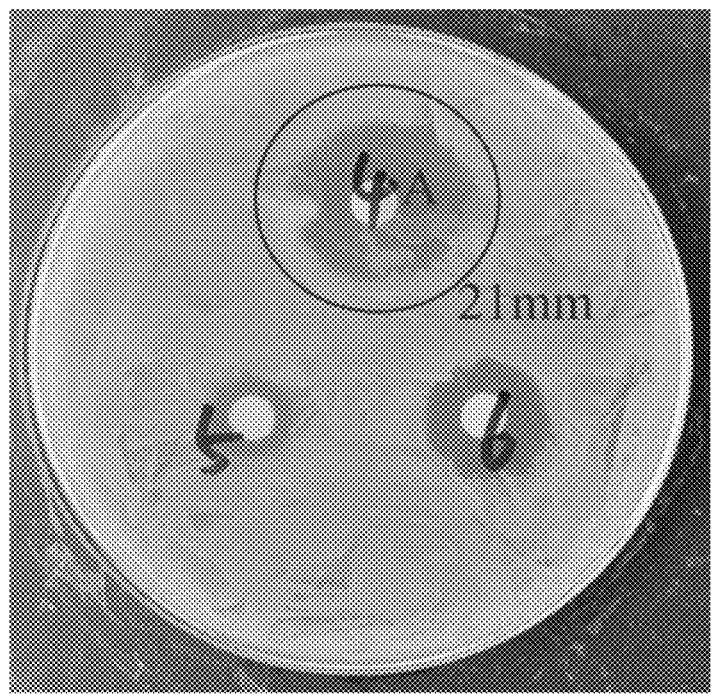
FIG. 1 shows the in vitro antibacterial activity of pleuromutilin 2-[(diphenylmethyl)thio]acetic acid ester against drug-resistant bacteria MRSA 18-171.

Reference will now be made in detail to embodiments of the present invention, example of which is illustrated in the accompanying drawings. The following examples illustrate the present invention, but the present invention is not limited to the following examples.

Example 1

Preparation of pleuromutilin 2-[(diphenylmethyl)thio]acetic acid ester (the Compound of Formula I) ((1R,2R,4S,5S,6R,7S,8R,11R)-11-formyl-5-hydroxy-1,4,6,7,8-pentamethyl-4-vinylbicyclo[5.3.1]undecan-2-yl 2-(2-(benzhydrylthio)acetoxy)acetate)

In a 100 mL three-necked flask, 378.5 mg (1 mmol) of pleuromutilin and 10.1 mg (0.1 mol) of triethylamine were dissolved in 25 mL of dichloromethane under nitrogen atmosphere. 303.6 mg (1.1 mmol) of 2-[(diphenylmethyl)thio]acetic acid chloride (compound of formula III) was dissolved in 10 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 482.0 mg of the title compound, a yield of 79.5%.

$^1$H-NMR (400 MHz, Chloroform-d) δ (ppm): 7.51 (4H, d), 7.37 (4H, d), 7.31 (2H, d), 7.29 (1H, d), 6.57 (1H, t), 5.84 (1H, s), 5.53 (1H, d), 5.39 (2H, s), 5.24 (1H, d), 4.54 (1H, t), 4.02 (1H, d), 3.42 (1H, d), 3.21 (2H, s), 2.40 (1H, s), 1.72-1.39 (11H, t), 1.23 (6H, d), 0.95 (3H, d), 0.82 (3H, t); $^{13}$C-NMR (100 MHz, Chloroform-d) δ ppm): 216.8, 169.5, 166.3, 165.9, 140.2, 138.8, 128.6, 128.5, 127.4, 117.3, 74.6, 70.6, 69.8, 58.1, 53.9, 41.5, 36.7, 26.8, 24.8, 16.7, 16.6, 14.8, 11.5.

Example 2

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of toluene under nitrogen atmosphere.

331.2 mg (1.2 mmol) of 2-[(diphenylmethyl)thio]acetic acid chloride was dissolved in 10 mL of toluene, and added dropwise to the reaction mixture by a separatory funnel. After the completion of the dropwise addition, the reaction was carried out at 30° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 3:1 as eluent, and the eluent was combined and concentrated under reduced pressure to obtain 456.5 mg of the title compound, a yield of 75.3%.

Example 3

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dimethylformamide under nitrogen atmosphere. 358.8 mg (1.3 mmol) of 2-[(diphenylmethyl)thio]acetic acid chloride was dissolved in 15 mL of dimethylformamide, and added dropwise to the reaction mixture by a separatory funnel. After the completion of the dropwise addition, the reaction was carried out at 40° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 403.8 mg of the title compound, a yield of 66.6%.

Example 4

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dichloromethane under nitrogen atmosphere. 303.6 mg (1.1 mmol) of 2-[(diphenylmethyl)thio]acetic acid chloride was dissolved in 10 mL of dichloromethane, and added dropwise to the reaction mixture by a separatory funnel. After the completion of the dropwise addition, the reaction was carried out at 25° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 3:1 as eluent, and the eluent was combined and concentrated under reduced pressure to obtain 452.6 mg of the title compound, a yield of 70.2%.

Example 5

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dimethylformamide under nitrogen atmosphere. 331.2 mg (1.2 mmol) of 2-[(diphenylmethyl)thio]acetic acid chloride was dissolved in 15 mL of dimethylformamide, and added dropwise to the reaction mixture by a separatory funnel. After the completion of the dropwise addition, the reaction was carried out at 50° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 425.9 mg of the title compound, a yield of 68.6%.

Example 6

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of toluene under nitrogen atmosphere. 358.8 mg (1.3 mmol) of 2-[(diphenylmethyl)thio]acetic acid chloride was dissolved in 15 mL of toluene, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 415.5 mg of the title compound, a yield of 67.7%.

Example 7

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dimethylformamide under nitrogen atmosphere. 303.6 mg (1.1 mmol) of 2-[(diphenylmethyl)thio]acetic acid chloride was dissolved in 15 mL of dimethylformamide, and added dropwise to the reaction mixture by a separatory funnel. After the completion of the dropwise addition, the reaction was carried out at 30° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 445.3 mg of the title compound, a yield of 71.8%.

Example 8

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dichloromethane under nitrogen atmosphere. 331.2 mg (1.2 mmol) of 2-[(diphenylmethyl)thio]acetic acid chloride was dissolved in 15 mL of dichloromethane, and added dropwise to the reaction mixture by a separatory funnel. After the completion of the dropwise addition, the reaction was carried out at 25° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 443.2 mg of the title compound, a yield of 73.1%.

Example 9

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of toluene under nitrogen atmosphere. 358.8 mg (1.3 mmol) of 2-[(diphenylmethyl)thio]acetic acid chloride was dissolved in 15 mL of toluene, and added dropwise to the reaction mixture by a separatory funnel. After the completion of the dropwise addition, the reaction was carried out at 30° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 391.1 mg of the title compound, a yield of 64.5%.

Example 10

Preparation of pleuromutilin 2-[(diphenylmethyl)thio]acetic acid ester

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dichloromethane under nitrogen atmosphere. 303.6 mg (1.1 mmol) of 2-[(diphenylmethyl)thio]acetic acid chloride was dissolved in 15 mL of dichloromethane, and added dropwise to the reaction mixture by a separatory funnel. After the completion of the dropwise addition, the reaction was carried out at 35° C. for 4 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 440.2 mg of the title compound, a yield of 72.6%.

Example 11

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of dimethylformamide under nitrogen atmosphere. 331.2 mg (1.2 mmol) of 2-[(diphenylmethyl)thio]acetic acid chloride was dissolved in 15 mL of dimethylformamide, and added dropwise to the reaction mixture by a separatory funnel. After the completion of the dropwise addition, the reaction was carried out at 30° C. for 5 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 3:1 as eluent, and the eluent was combined and concentrated under reduced pressure to obtain 398.3 mg of the title compound, a yield of 65.7%.

Example 12

Preparation of pleuromutilin 2-[(diphenylmethyl)thio]acetic acid ester

In a 100 mL three-necked flask, 378.5 mg (1 mmol) of pleuromutilin and 10.1 mg (0.1 mol) of triethylamine were dissolved in 25 mL of toluene under nitrogen atmosphere. 358.8 mg (1.3 mmol) of 2-[(diphenylmethyl)thio]acetic acid chloride was dissolved in 15 mL of toluene, and added dropwise to the reaction mixture by a separatory funnel. After the completion of the dropwise addition, the reaction was carried out at 20° C. for 6 hours. Thin layer chromatography was used to track the reaction to completion, heating was stopped, and the protective device was removed. The reaction mixture was concentrated, washed in water, extracted with ethyl acetate, concentrated and dried to obtain a crude product. The crude product was purified by silica gel column chromatography with petroleum ether:ethyl acetate 4:1 as eluent, and the eluent was combined and concentrated under reduced pressure to obtain 419.6 mg of the title compound, a yield of 69.2%.

Example 13

Preparation of pleuromutilin 2-[(diphenylmethyl)thio]acetic acid ester

In a 250 mL three-necked flask, 378.5 mg (1 mmol) of pleuromutilin, 284.2 mg (1.1 mmol) of 2-[(diphenylmethyl)thio]acetic acid and 18.4 mg (0.01 mmol) silicomolybdic acid were dissolved in 150 mL of 1-butyl-3-methylimidazolium tetrafluoroborate under nitrogen atmosphere. After full dissolution, the temperature of the reaction mixture was raised to 30° C. and the reaction was carried out for 6 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 517.2 mg of the title compound, a yield of 85.3%.

Example 14

Preparation of pleuromutilin 2-[(diphenylmethyl)thio]acetic acid ester

In a 250 mL three-necked flask, 378.5 mg (1 mmol) of pleuromutilin, 315.0 mg (1.2 mmol) of 2-[(diphenylmethyl)thio]acetic acid and 18.4 mg (0.01 mmol) silicomolybdic acid were dissolved in 150 mL of 1-butyl-3-methylimidazolium tetrafluoroborate under nitrogen atmosphere. After full dissolution, the temperature of the reaction mixture was raised to 25° C. and the reaction was carried out for 4 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 479.6 mg of the title compound, a yield of 79.1%.

Example 15

Preparation of pleuromutilin 2-[(diphenylmethyl)thio]acetic acid ester

In a 250 mL three-necked flask, 378.5 mg (1 mmol) of pleuromutilin, 335.8 mg (1.3 mmol) of 2-[(diphenylmethyl)thio]acetic acid and 18.4 mg (0.01 mmol) silicomolybdic acid were dissolved in 150 mL of 1-hexyl-3-methylimidazolium tetrafluoroborate under nitrogen atmosphere. After full dissolution, the temperature of the reaction mixture was raised to 35° C. and the reaction was carried out for 5 hours. Thin layer chromatography was used to track the reaction to completion, heating was stopped, and the protective device was removed. The reaction mixture system was allowed to separate into layers to give a crude product. 1-Hexyl-3-methylimidazolium tetrafluoroborate was recovered. The crude product was recrystallized with 30 mL methanol and dried to obtain 488.0 mg of the title compound, a yield of 80.5%.

Example 16

Preparation of pleuromutilin 2-[(diphenylmethyl)thio]acetic acid ester

In a 250 mL three-necked flask, 378.5 mg (1 mmol) of pleuromutilin, 284.2 mg (1.1 mmol) of 2-[(diphenylmethyl)thio]acetic acid and 18.4 mg (0.01 mmol) silicomolybdic acid were dissolved in 150 mL of 1-butyl-3-methylimidazolium tetrafluoroborate under nitrogen atmosphere. After full dissolution, the temperature of the reaction mixture was raised to 30° C. and the reaction was carried out for 5 hours. Thin layer chromatography was used to track the reaction to completion, heating was stopped, and the protective device was removed. The reaction mixture system was allowed to separate into layers to give a crude product. 1-Butyl-3-methylimidazolium tetrafluoroborate was recovered. The crude product was recrystallized with 30 mL methanol and dried to obtain 480.2 mg of the title compound, a yield of 79.2%.

Example 17

Antibacterial Activity Test of the Compounds of the Invention

The antimicrobial efficacy was determined by a paper diffusion method drug sensitivity test.

Experimental strains: multi-resistant *Staphylococcus aureus* 171, multi-resistant *Staphylococcus aureus* 575, multi-resistant *Staphylococcus aureus* 596. The experimental strains were provided by Huashan Hospital Affiliated to Fudan University (Institute of Antibiotic of Fudan University).

Drug sensitive paper: The drug sensitive paper is a special drug sensitive paper with a diameter of 6.35 mm and a water absorption of 0.02 mL. The control drug was vancomycin (30 μg/tablet); the test drug was pleuromutilin 2-[(diphenylmethyl)thio]acetic acid ester (30 μg/tablet).

Reagents: LB agar medium, LA broth medium, dichloromethane.

Equipment: Ultra-clean workbench, high-pressure sterilization pot, gas bath constant temperature shaking incubator.

Preparation of Bacterial Suspension:

The experimental strains were inoculated in non-selective medium and placed in air at 37° C. for 24 h. Pick a single colony that grows well and inoculate it into broth medium, incubate at 35° C.±2° C. for 6 hours, and use LA broth medium to calibrate the concentration of the bacterial solution to 0.5 Mie turbidimetric tube ($1.5 \times 15^8$ CFU/mL). A bacterial suspension is obtained.

Paper Diffusion Method Drug Sensitivity Test:

LB dry powder was weighed, sterilized at 103.4 Kpa, 121.3° C. high-pressure steam for 15 min, and then placed it in a 40° C.-50° C. water bath. A sterile empty plate (inner diameter 9 cm) was placed on the surface of the ultra-clean table water table, and LB dry powder was poured to the plate. The thickness of each plate was 3 mm to 4 mm. After the plate was cooled at room temperature, it was stored in the refrigerator at 2° C.-8° C. A sterile cotton swab was used to dip the bacterial solution and to evenly coat the surface of the LB plate 3 times. After inoculation of the bacterial suspension, the LB plate was dried at room temperature for 3 min to 5 min. Sterile forceps were used to closely attach the antibacterial drug paper to the dish. The dish was put upside down and placed in a 37° C. incubator for 24 h. The results were observed by measuring the diameter. Taking 0.5% DMSO solution as a negative control, the antibacterial activity is expressed by the diameter of the inhibition zone. The inhibition zone ≥17 mm, sensitive; the inhibition zone of 15 mm-16 mm, intermediary; the inhibition zone ≤14 mm, drug resistance.

Figure 2:
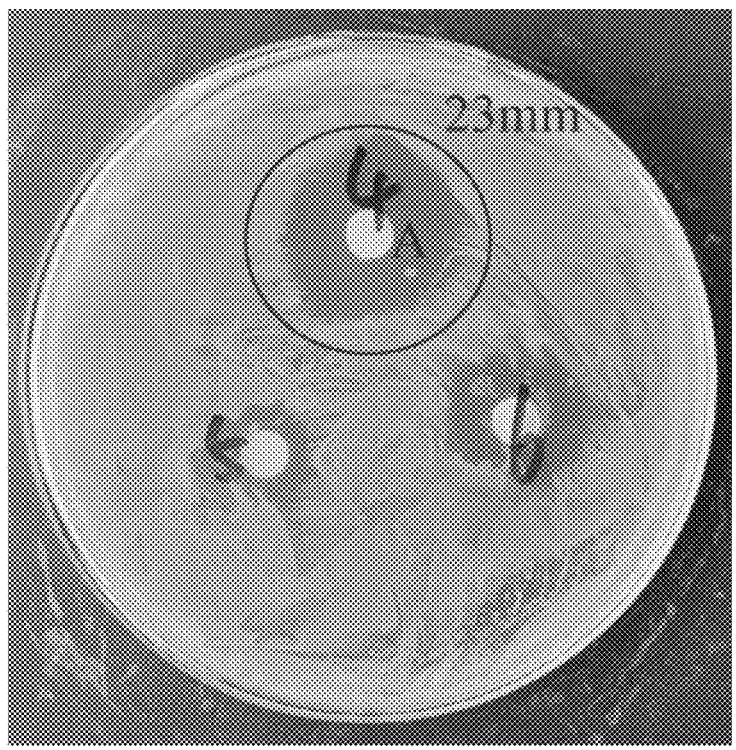
FIG. 2 shows the in vitro antibacterial activity of pleuromutilin 2-[(diphenylmethyl)thio]acetic acid ester against drug-resistant bacteria MRSA 18-575.
Figure 3:
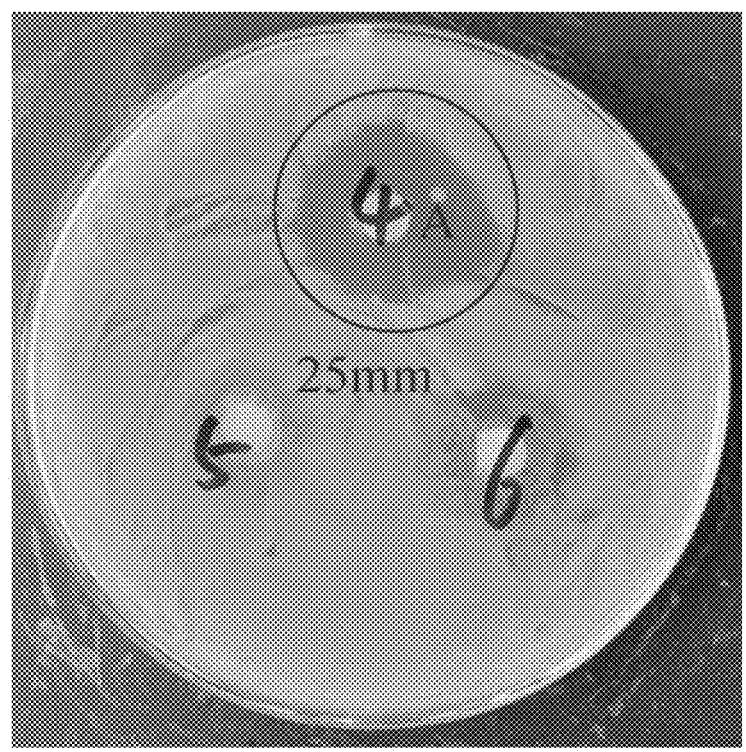
FIG. 3 shows the in vitro antibacterial activity of pleuromutilin 2-[(diphenylmethyl)thio]acetic acid ester against drug-resistant bacteria MRSA 18-596.

In FIGS. 1-3, pleuromutilin 2-[(diphenylmethyl)thio]acetic acid ester is represented by the letter A. FIG. 1 shows the antibacterial effect of pleuromutilin 2-[(diphenylmethyl)thio]acetic acid ester on MRSA 18-171. FIG. 2 shows the antibacterial effect of pleuromutilin 2-[(diphenylmethyl)thio]acetic acid ester on MRSA 18-575. FIG. 3 shows the antibacterial effect of pleuromutilin 2-[(diphenylmethyl)thio]acetic acid ester on MRSA 18-596. The results are also shown in Table 1.

TABLE 1

Experimental results of the zone of inhibition

| Compound | Zone of inhibition/mm Strain | | |
|---|---|---|---|
| | MRSA 18-171 | MRSA 18-575 | MRSA 18-596 |
| Vancomycin | 17 | 18 | 21 |
| Pleuromutilin | 0 | 0 | 0 |
| 2-[(Diphenylmethyl)thio] acetic acid | 0 | 0 | 0 |
| Pleuromutilin 2-[(diphenylmethyl)thio] acetic acid ester | 21 | 23 | 25 |

The results in FIGS. 1-3 and Table 1 show that pleuromutilin and 2-[(diphenylmethyl)thio]acetic acid have no inhibitory effect on drug-resistant bacteria. Pleuromutilin 2-[(diphenylmethyl)thio]acetic acid ester has strong inhibitory effects on MRSA 18-171, 18-575, 18-596, and the diameter of bacteriostatic zone against multidrug resistant *Staphylococcus aureus* 18-596 was up to 25 mm. In summary, pleuromutilin 2-[(diphenylmethyl)thio]acetic acid ester of the present invention can be used as an antibacterial drug candidate for multi-drug resistant *Staphylococcus aureus*, and further preclinical studies can be conducted.

What is claimed is:

1. A compound with anti-drug resistant bacteria activity having the following formula

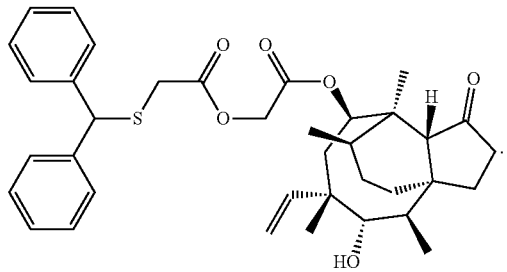

(I)

2. A method of preparing the compound of formula (I) of claim 1, comprising:
   reacting a compound of formula (II) with a compound of formula (III) to obtain the compound of formula (I),

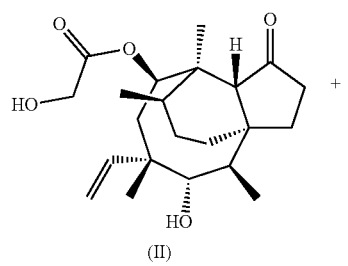

(II)

+

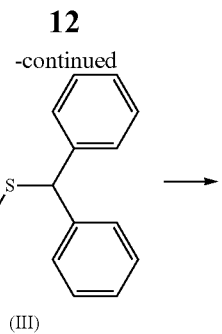

(III)

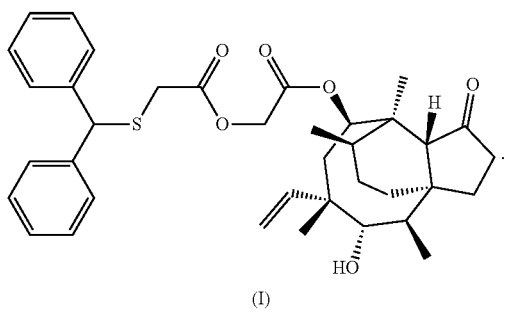

(I)

3. The method of claim 2, wherein the reaction of the compound of formula (II) with the compound of formula (III) comprises the following steps:
   placing the compound of formula (II) and the compound of formula (III), in a molar ratio of 1:1 to 1:1.3, in a reactor;
   adding an organic solvent and a catalytic amount of triethylamine under a nitrogen atmosphere to obtain a reaction mixture;
   heating the reaction mixture at 20-60° C. for 3-6 hours;
   extracting the reaction mixture with ethyl acetate to obtain a crude product; and
   purifying the crude product on a silica gel chromatography column with petroleum ether and ethyl acetate as an eluent to obtain the compound of formula (I).

4. The method of claim 3, wherein the organic solvent is selected from the group consisting of toluene, dichloromethane and N,N-dimethylformamide.

5. The method of claim 4, wherein the organic solvent is dichloromethane.

6. The method of claim 3, wherein the molar ratio of the compound of formula (II) and the compound of formula (III) is 1:1.1.

7. The method of claim 3, wherein the reaction mixture is heated at 25° C.

8. The method of claim 3, wherein the reaction mixture is heated for 5 hours.

9. The method of claim 3, wherein the eluent is petroleum ether:ethyl acetate=4:1.

10. A method of preparing the compound of formula (I) of claim 1, comprising:
    reacting a compound of formula (II) with a compound of formula (IV) to obtain the compound of formula (I):

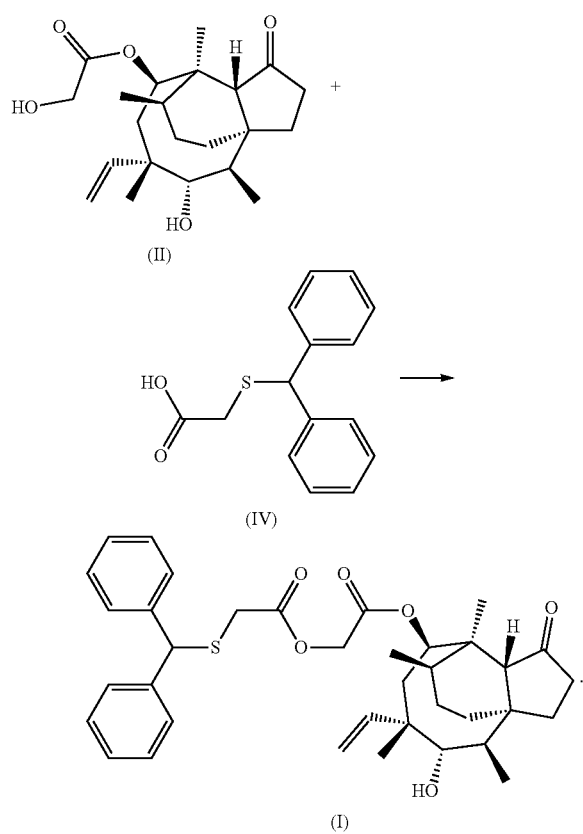

11. The method of claim 10, wherein the reaction of the compound of formula (II) with the compound of formula (IV) comprises the following steps:
placing the compound of formula (II), a catalyst, and an ionic liquid in a reactor under nitrogen atmosphere, the catalyst being 12-molybdosilicic acid hydrate of formula $H_6Mo_{12}O_{41}Si$;
adding the compound of formula (IV) to the reactor to form a reaction mixture;
heating the reaction mixture at 20-50° C. for 4-8 hours;
placing the reaction mixture in a separating funnel to separate a crude product;
purifying the crude product by recrystallization in methanol to obtain the compound of formula (I); and
recycling the ionic liquid.

12. The method of claim 11, wherein the ionic liquid is selected from the group consisting of 1-octyl-3-methylimidazolium and hexafluorophosphate, 1-hexyl-3-methylimidazolium tetrafluoroborate and 1-butyl-3-methylimidazolium tetrafluoroborate of formula [BMIM][BF4].

13. The method of claim 12, wherein the ionic liquid is 1-butyl-3-methylimidazolium tetrafluoroborate.

14. The method of claim 11, wherein the compound of formula (II) and the compound (IV) have a molar ratio of 1:1 to 1:1.3.

15. The method of claim 14, wherein the molar ratio of the compound of formula (II) and the compound of formula (IV) is 1:1.1.

16. The method of claim 11, wherein the reaction mixture is heated at 30° C.

17. The method of claim 11, wherein the reaction mixture is heated for 6 hours.

* * * * *